US012773476B2

(12) United States Patent
Deister

(10) Patent No.: US 12,773,476 B2
(45) Date of Patent: Oct. 27, 2026

(54) TISSUE REPAIR MEMBRANE AND METHODS FOR PREPARING THE SAME

(71) Applicant: Axogen Corporation, Alachua, FL (US)

(72) Inventor: Curt Deister, Riverview, FL (US)

(73) Assignee: Axogen Corporation, Alachua, FL (US)

(*) Notice: Subject to any disclaimer, the term of this patent is extended or adjusted under 35 U.S.C. 154(b) by 0 days.

(21) Appl. No.: 19/538,501

(22) Filed: Feb. 12, 2026

(65) Prior Publication Data

US 2026/0174933 A1 Jun. 25, 2026

Related U.S. Application Data

(63) Continuation of application No. 16/992,857, filed on Aug. 13, 2020, now Pat. No. 12,576,190.

(60) Provisional application No. 62/887,146, filed on Aug. 15, 2019.

(51) Int. Cl.

| | |
|---|---|
| ***A61L 27/52*** | (2006.01) |
| ***A61L 27/20*** | (2006.01) |
| ***A61L 27/34*** | (2006.01) |
| ***A61L 27/36*** | (2006.01) |
| ***C08L 5/08*** | (2006.01) |

(52) U.S. Cl.

CPC ............... *A61L 27/52* (2013.01); *A61L 27/20* (2013.01); *A61L 27/34* (2013.01); *A61L 27/3629* (2013.01); *A61L 27/3675* (2013.01); *A61L 27/3687* (2013.01); *C08L 5/08* (2013.01); *A61L 2420/02* (2013.01); *A61L 2420/08* (2013.01); *A61L 2430/32* (2013.01); *C08L 2203/02* (2013.01)

(58) Field of Classification Search

CPC .......... A61L 27/52; A61L 27/20; A61L 27/34; A61L 27/3629; A61L 27/3687; A61L 2420/02; A61L 2430/32; C08L 5/08; C08L 2203/02

See application file for complete search history.

(56) References Cited

U.S. PATENT DOCUMENTS

| | | | |
|---|---|---|---|
| 11,980,700 B2 | 5/2024 | Zawko et al. | |
| 2001/0031974 A1 | 10/2001 | Hadlock et al. | |
| 2004/0048796 A1 | 3/2004 | Hariri et al. | |
| 2010/0179645 A1 | 7/2010 | Chen et al. | |
| 2012/0088832 A1 | 4/2012 | Mayes et al. | |
| 2015/0250923 A1* | 9/2015 | Lyngstadaas | A61L 27/52 514/21.3 |
| 2015/0320915 A1 | 11/2015 | Schmidt et al. | |
| 2016/0243281 A1 | 8/2016 | Leach | |

FOREIGN PATENT DOCUMENTS

| | | | | |
|---|---|---|---|---|
| CN | 107397980 A | | 11/2017 | |
| JP | 2001519210 A | | 10/2001 | |
| JP | 2014518879 A | | 8/2014 | |
| JP | 2018521696 A | | 8/2018 | |
| KR | 101766679 B1 | | 8/2017 | |
| WO | WO-0154593 A1 | * | 8/2001 | A61B 17/1128 |
| WO | 2007005807 A2 | | 1/2007 | |
| WO | 2014038885 A1 | | 3/2014 | |
| WO | 2015050943 A1 | | 4/2015 | |
| WO | 2016143746 A1 | | 9/2016 | |
| WO | 2016168669 A1 | | 10/2016 | |
| WO | 2018131517 A1 | | 7/2018 | |
| WO | WO 2018/121630 A1 | * | 7/2018 | A61L 27/40 |

OTHER PUBLICATIONS

Liu et al. (In Situ Sodium Alginate-Hyaluronic Acid Hydrogel Coating Method for Clinical Applications, Macromolecular Research, 2014 (Year: 2014).*

WO 2018/121630 A1 translated (Year: 2018).*

Diamond, Michael P., et al. "Seprafilm® adhesion barrier: (1) a review of preclinical, animal, and human investigational studies." Gynecological Surgery, 9.3 (2012): 237-245.

Dunn et al. (Lubricity of Surface Hydrogel Layers, Tribol Letter 2013).

International Search Report and Written Opinion issued on Dec. 2, 2020 in counterpart International Patent Application No. PCT/US2020/046309 (27 pages).

Kim, Seon Jeong, et al. "Synthesis and characteristics of polyelectrolyte complexes composed of chitosan and hyaluronic acid." Journal of Applied Polymer Science, 91.5 (2003): 2908-2913.

Li et al., "Biodegradable and injectable in situ cross-linking chitosan-hyaluronic acid based hydrogels for postoperative adhesion prevention", Biomaterials, 2014, vol. 35: pp. 3903-3917.

Majcher et al. (Hydrogel Synthesis and Design, Functional Biopolymers, 2018).

Na et al., (Hyaluronic acid/mildly crosslinked alginate hydrogel as an injectable tissue adhesion barrier, J Mater Sci: Mater Med 2012).

Samorezov et al. (Dual Ionic and Photo-Crosslinked alginate hydrogels for micropatterned spatial control of material properties and cell behavior. Bioconjug Chem Jul. 15, 2015).

Machine translation of WO-2014038885-A1, Mar. 13, 2014 (Year: 2014).

* cited by examiner

*Primary Examiner* — Robert A Wax
*Assistant Examiner* — John Seungjai Kwon
(74) *Attorney, Agent, or Firm* — Bookoff McAndrews, PLLC

(57) ABSTRACT

Provided herein is a tissue repair matrix modified with a hydrogel polymer to provide adhesion and/or lubrication to assist with the use and implantation of the tissue repair membrane, and to facilitate healing and/or avoid or minimize damage to adjacent, e.g., tissues, during or after implantation.

29 Claims, 9 Drawing Sheets

TISSUE REPAIR MEMBRANE AND METHODS FOR PREPARING THE SAME

CROSS REFERENCE TO RELATED APPLICATIONS

This patent application is a continuation of and claims the benefit of priority to U.S. application Ser. No. 16/992,857, filed on Aug. 13, 2020, which claims the benefit of priority to U.S. Provisional Application No. 62/887,146, filed on Aug. 15, 2019, the entireties of which are incorporated herein by reference.

TECHNICAL FIELD

The present disclosure generally relates treatment of damaged tissue. More specifically, the present disclosure relates to membranes that can be employed to reinforce, protect or treat damaged tissue, and provide adhesiveness and/or lubrication to the membrane.

BACKGROUND ART

Injury to the nervous system, both central nervous system (CNS) and the peripheral nervous system (PNS), can be caused by physical injury, neurological disorders, certain medical procedures or therapies, ischemia, tumors, metabolic or nutritional disorders, cognition or mood disorders, exposure to chemicals or drugs, infections, and various diseases. The period for recovery from injuries to the nervous system is often extensive because axon regeneration is limited to a few millimeters a day and significant levels of growth inhibitors can be present. There remains a need to develop effective treatments and methods that can assist nerve regeneration after injury.

A known method of treatment of nerve damage employs surrounding or wrapping the injured nerve with a membrane that is typically secured by sutures, or microclips, during surgery. This procedure requires additional medical devices (e.g., suture or clips), requires additional operating time, and can require significant microsurgical skill, particularly when sutures are employed. Additionally, the procedure and additional materials used for the securing (e.g., suture knot and/or microclips) can increase potential trauma to the nerve and surrounding tissue and the likelihood of adhesions due to reactions to the securing device material.

There are several existing membrane products that can be used in the treatment of nerve damage, such as SepraFilm. SepraFilm is an adhesion barrier membrane that is a sterile, bioresorbable, translucent adhesion barrier comprised of two anionic polysaccharides, namely sodium hyaluronate and carboxymethylcellulose. Additionally there are also amniotic sac-based products available. A significant disadvantage of these products is that they are mechanically weak and so cannot be effectively manipulated in the surgical field. This mechanical weakness also prevents them from being mechanically secured, since the devices also are not strongly adhered to the nerve, there can also be a risk of migration after placement and resultant failure of the protective procedure.

SUMMARY

The present disclosure relates to a device which may be capable of surrounding injured tissue, may be self-adhesive, and may also be capable of providing lubrication to reduce undesired interaction, e.g., friction, with surrounding or adjacent matter, e.g., tissue.

Additionally, the present disclosure may reduce the number of products/components needed for securing the damaged tissue in some use cases.

Consistent with some aspects of the present disclosure, surgical procedures may be simplified and the total surgical time may be decreased through the use of the disclosed devices.

In some embodiments, the present disclosure may allow a reduction in the potential for fibrosis, and complications from fastening/securing devices currently employed in tissue repair, such as sutures and clips.

In some implementations consistent with the present disclosure, self-adhesion of a tissue repair membrane, with minimal adhesion to surrounding or adjacent matter, e.g., tissue, may significantly ease the administration of the tissue repair membrane and consequently the overall tissue repair. This may result in more control, adaptability and flexibility for surgeons because the surgeon may be able to adjust the positioning of the membrane during surgery to better surround/support the damaged tissue. The surgeon may be able to adjust the positioning of the membrane multiple times, as opposed to a single time (because of the current requirement to fix the membrane onto the damaged tissue with sutures or other fastening devices).

In some embodiments, the present disclosure may provide self-adhesion capability to the tissue repair membrane by adding a surface layer of a biocompatible hydrogel material. In some example embodiments, the hydrogel material may exhibit low cell adhesion properties, and may add minimal, if any, bulk effects to the tissue repair membrane.

In some embodiments, the tissue repair membrane may be modifiable (chemically or physically) to accept the biocompatible hydrogel material. In some embodiments, the tissue repair membrane may be able to be linked with a material that is a poly-anionic and/or poly-cationic.

In an example embodiment consistent with the present disclosure a tissue repair membrane may be treated with a hydrophilic material to provide an adhesive and lubricating surface to the tissue repair membrane. In an example embodiment, the tissue repair membrane may be a nerve protective membrane. In some embodiments consistent with the present disclosure gliding of the membrane relative to surrounding or adjacent matter, e.g., tissue, may be improved and soft tissue attachments to the membrane may be reduced. The lubrication may also increase a surgeon's options for early or late mobilization.

An example biocompatible hydrogel material may include hyaluronic acid. Hyaluronic acid is an anionic, nonsulfated glycosaminoglycan distributed widely throughout connective, epithelial, and neural tissues. Human synovial hyaluronic acid ranges from about 3 to 7 million Daltons per molecule. In some embodiments, the use of hyaluronic acid may improve the remodeling characteristics of the membrane.

In an example embodiment, the present disclosure may employ bonding of the biocompatible hydrogel material to the tissue repair membrane. In an example embodiment, the present disclosure may provide covalent bonding of the biocompatible hydrogel material and the tissue repair membrane. This can be accomplished by using a tissue repair membrane that possesses chemical linkages on the exterior surface of the membrane that will allow it to covalently bond with the biocompatible hydrogel material. Some embodiments consistent with the present disclosure may provide methods for modifying a tissue membrane to add suitable chemical linking groups. In an example embodiment, the membrane may contain primary amines, or other aldehyde reactive groups that can covalently bond with suitable linking groups on the biocompatible hydrogel material. The biocompatible hydrogel material may also be incorporated into the underlying tissue repair membrane through interpenetration of the polymer chains, e.g. physical binding. The bonding of the tissue repair membrane and the biocompatible hydrogel material may provide for a tighter hold of the coating onto the membrane than would be possible with non-bonding coatings.

Additionally, the biocompatible hydrogel material, such as hyaluronic acid or equivalent materials, may provide lubrication to the membrane relative to surrounding or adjacent matter, e.g., tissue, because of its hydrophilic nature. Similar equivalent materials may include alginate, chondroitin sulfate, dermatan sulfate, or similar glycosaminoglycans and related polymers.

Some embodiments consistent with the present disclosure may provide for incorporation of poly-cationic and poly-anionic surface regions onto the surface of the tissue repair membrane. These regions may form poly-electrolyte complexes when they are brought into contact with each other. This interaction between positive and negative charged groups may provide for adhesion of the membrane to itself (e.g., with only limited adhesion to surrounding tissue in some embodiments).

The present disclosure can have varying degrees of coating of the poly-anionic and poly-cationic on the tissue repair membrane. Levels of coatings from 1:99 poly-anionic/cationic to 99:1 poly-anionic/cationic are within the scope of the present disclosure. In one example embodiment the poly-anionic coating may be employed over the majority of the membrane area. This may allow for adhesion with the poly-cationic regions, and also a high degree of lubrication with respect to tissue that the tissue repair membrane may be applied to, because of decreased friction and/or adhesiveness of the membrane to surrounding or adjacent matter, e.g., tissue, while still allowing the membrane to adhere to itself.

The present disclosure may provide methods for applying the hydrogel material to the tissue repair membrane.

The present disclosure may provide benefits for all types of tissue repair. Types of tissue that may be suitable for the present invention include nerve tissue, muscle tissue, tendons, ligaments, skin tissue, cardiac tissue, vascular tissue, dura tissue, fascia tissue, serosal tissue surrounding organs, or periostium.

The present invention is not limited to human use and will also be compatible with veterinary use.

DETAILED DESCRIPTION OF EXAMPLE EMBODIMENTS

Figure 1:
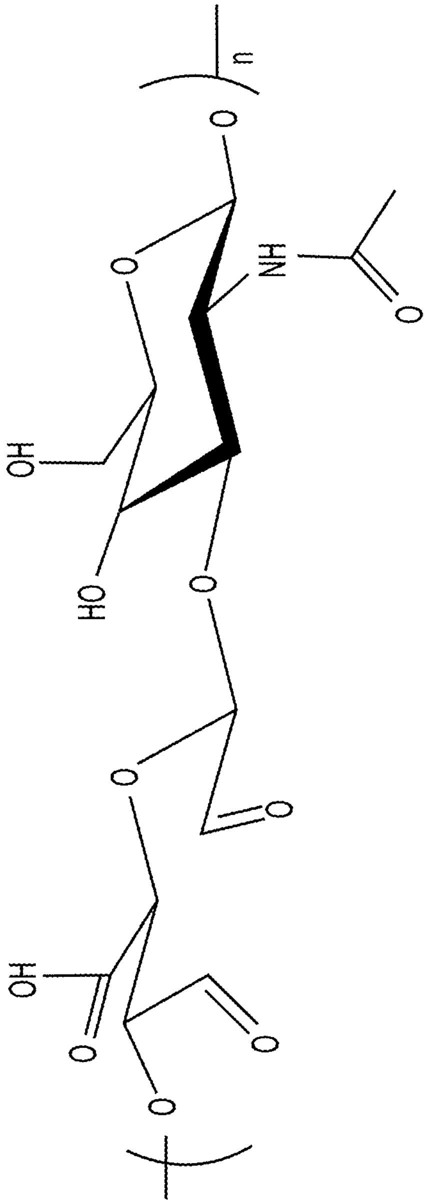
FIG. 1 is an illustrative example of "aldehyde HA" structure, according to an example embodiment.

A description of embodiments consistent with the present disclosure will now be given. It is expected that the present disclosure may take many other forms and shapes, hence the following disclosure is intended to be illustrative and not limiting, and the scope of the disclosure should be determined by reference to the appended claims.

Examples of the suitable hydrogel materials may include, but are not limited to, poly-anion polymers (net negative charge to the polymer) extracellular matrix components such as chondroitin sulfate and hyaluronic acid. These materials are typically highly hydrophilic polysaccharides with a relatively high degree of biocompatibility because both materials are members of the native extracellular matrix. Suitable polymers may be poorly cell adhesive. Cell membranes may typically have a negative charge potential (typical values for most cells in the −40 to −80 m V range), and therefore, negatively charged polymers, such as chondroitin sulfate and hyaluronic acid or equivalents thereof, will generally not adhere (or only weakly) to cellular tissue. Additionally, this may be one of the means by which the lubrication benefits of the hydrogel polymer may be provided.

Hyaluronic acid may have complex, molecular weight driven interactions. In certain embodiments high molecular weight hyaluronic acid may provide anti-cell adhesive and may also block, and/or inhibit, cell migration. This may provide an additional barrier for the damaged tissue. In other embodiments low molecular weight hyaluronic acid can act as a pro-angiogenic factor.

Additional anionic polymer materials may be selected from, but are not limited to, chondroitin, alginate, oxidized cellulose, particularly, non-regenerated oxidized cellulose (wherein the grade of oxidized cellulose contains both carboxylic acid and aldehyde groups); heparin, and sulfated versions of the prior polymers, and combinations thereof.

Additional cationic polymer materials may be selected from, but are not limited to, poly-lysine, poly-ornithine, polyhexamethylene biguanide (PHMB), polyethyleneimine (PEI), diethylaminoethyl-dextran (DEAE-dextran), poly (amidoamine) (PAMAM), and quaternary ammonium versions of the prior polymers, and combinations thereof.

Tissue repair membranes suitable for use in connection with the present disclosure may be prepared from human tissue including cadaver tissue, animal tissue such as but not limited to porcine tissue and ruminant tissue, placental tissue, stem cell tissue, or combinations thereof.

According to other embodiments, various additional and/or alternative tissue repair membranes may be utilized, including both natural materials, as well as synthetic materials, such as but not limited to membranes of woven or non-woven collagen, polycaprolactone or polylactic acid fibers.

Membranes consistent with the present disclosure may be capable of accepting the hydrogel material by various procedures. One such procedure may include providing covalent linkages between aldehyde reactive groups and primary amines. Poly-cationic materials may also be bound to the membrane either via covalent bonding or other known methods.

Embodiments consistent with the present disclosure may employ oxidation procedures to break a fraction of the heterocyclic rings in the polysaccharide backbone of the hydrogel material (such as in hyaluronic acid) resulting in two aldehyde motifs, wherein the polymer itself may be maintained through the ether linkage of the original backbone.

Suitable example oxidation agents may include sodium periodate and lead tetraacetate. Alternately, the primary alcohol group may be partially oxidized to an aldehyde through the use of a TEMPO catalyst or equivalent chemistries.

FIG. 1 is a depiction of a hyaluronic acid monomer oxidized in preparation for linkage to a primary amine on the membrane surface (e.g., an example of "aldehyde HA" structure), consistent with an illustrative example embodiment.

Some embodiments consistent with the present disclosure may employ hydrogel polymers with varying degrees of substitution. An illustrative example level of substitution may be approximately 5%. Substitution levels between about 1% and about 100% are within the scope of the present disclosure.

Figure 2:
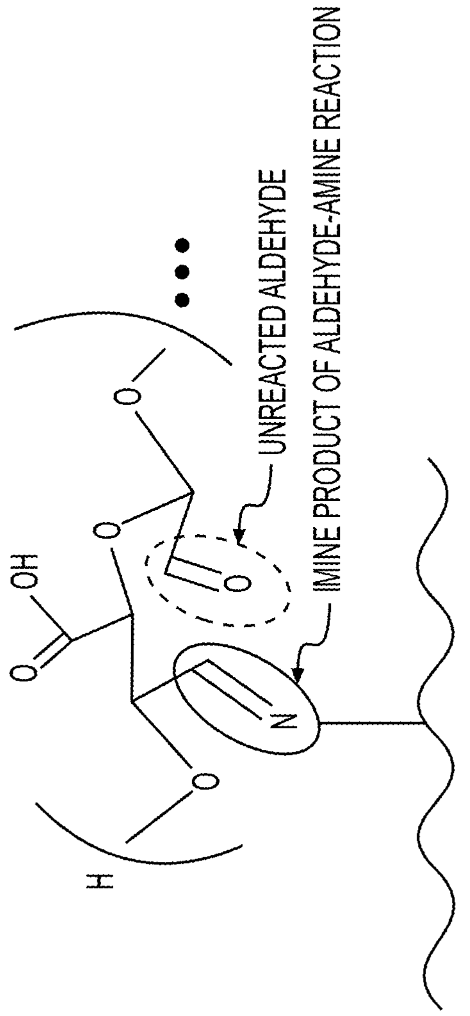
FIG. 2 is an illustrative example of aldehydes created in the backbone of the hydrogel polymer, according to an example embodiment.

As shown in FIG. 2, the aldehydes created in the backbone of the hydrogel polymer, such as in the hyaluronic acid shown above, may readily react with free amine groups present in protein-based membranes resulting in a tethering of the hyaluronic acid polymer to the membrane via imine bonds. Other bonding linkages are within the scope of the present disclosure. Examples of other linkages include peptide, ether, ester, and disulfide bonds through different chemistries.

Figure 3:
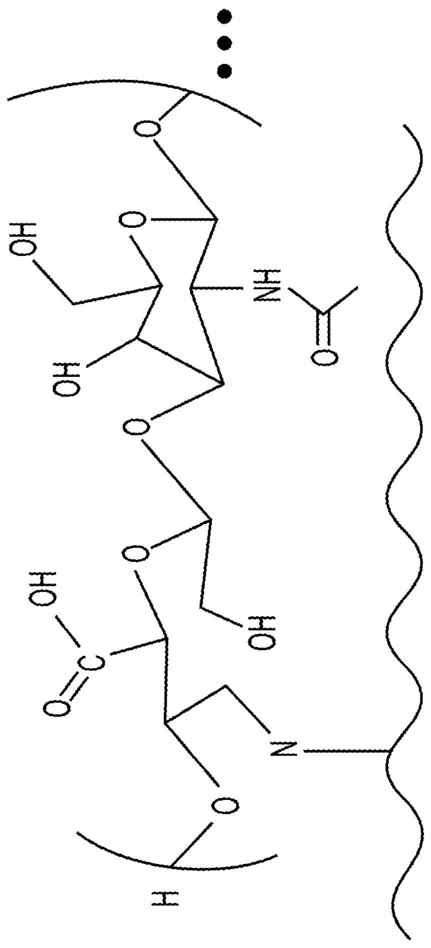
FIG. 3 is an illustrative example of imine residue (a non-covalently linked aldehyde motif) reduced with mild reducing agents, according to an example embodiment.

The imine residue (the non-covalently linked aldehyde motif) may then be reduced with mild reducing agents such as a cyanoborohydride, tri-acetoxy-bororhydride, or borohydride (especially the sodium salts of these ions), as shown in FIG. 3. Alternatively, even milder reducing agents such as formamide, solid zinc, ascorbic acid, sodium thiosulfate, and sodium dithionite may be useful in certain instances. Reducing the imine may help remove the associated color (e.g., typically a red-brown) and increase stability.

Reaction conditions may be carefully monitored and applied to restrict the modification to the hydrogel polymer and the membrane, and specifically to the areas of each material treated with the polymer.

Some embodiments consistent with the present disclosure may provide linkages between the hydrogel material and the tissue repair membrane. Certain embodiments may have a higher degree of linkage between the two components. In an illustrative example embodiment, a level of linkage may be approximately every monomer (100% modification) to every thousand monomers (0.1% modification) within the polymer. Other embodiments will have linkage approximately one in twenty (5%) to one in five (20%).

Other binding techniques between the hydrogel material and the membrane are within the scope of the present disclosure. The hydrogel material may be grafted onto the membrane surface via other known binding techniques. Possible techniques include, but are not limited to EDC/NHS ester, sulfhydryl/disulfide bonding, thio-ene reaction, maleimide, epoxide, imidoester, any "click" chemistry, or combinations thereof.

EDC (1-Ethyl-3-(3-dimethylaminopropyl)-carbodiimide) is a zero-length crosslinking agent used to couple carboxyl or phosphate groups to primary amines. EDC may be used to form amide bonds. To increase the stability of the EDC, N-hydroxysuccinimide (NHS) or N-hydroxysulfoxuccinimide (sulfo-NHS) may be used. The addition of Sulfo-NHS may stabilize the amine-reactive intermediate by converting it to an amine-reactive Sulfo-NHS ester, increasing the efficiency of EDC-mediated coupling reactions.

In one example embodiment, similar to the maleimide chemistry, the oxidation of the hyaluronic acid (discussed previously) may be continued until the aldehydes are converted to carboxylic acids. Due to the close spatial localization of the two carboxylic acids, they may mimic the activity in maleimide chemistry, whereby two carboxylic acid moieties attach to a single central carbon and generate an abnormally strong ionic bond with an amine.

Membranes with aldehyde reactive groups, such as primary amine, tertiary amines, quarternary amines, or substituents with similar chemical properties, may be incorporated into the present disclosure. These membranes may be similarly reacted with hydrogel materials forming bonds with the aldehyde groups, or equivalent binding substituents, to form a membrane/hydrogel polymer material suitable for use as a tissue repair membrane as described herein.

Additionally, physical binding may be obtained by soaking the membrane in a sol-gel prior to drying, resulting in an micro- or macro-scale interpenetrating polymer network (base membrane and hydrogel).

There are various methods that may be used to prepare the hydrogel polymer-membrane complex consistent with the present disclosure.

In one example embodiment, the membrane may be soaked in a solution of hydrogel polymer prior to drying and sterilization. Upon hydration the hydrogel polymer may be present on the surface of the membrane, as well as in the bulk of the membrane, and may provide similar functionality as described herein (adhesion and/or lubrication) but may not be covalently bound to the membrane. This may allow the hydrogel polymer to be retained at the surface of the membrane and may allow ease of migration and diffusion of the hydrogel polymer around the membrane. In such an example embodiment no reactive species may be needed between the hydrogel polymer and the membrane, as the binding interaction may be physical intertangling of the polymer chains. If alginate or another ionic cross-linking polymer is present, this physical intertangling effect can be further increased by introducing calcium ions to ionically cross-link the polymer component.

In another illustrative example embodiment, prior to complexation with the membrane, the hydrogel polymer may be partially oxidized to create reactive groups within certain monomers of the polymer chain. In one embodiment hyaluronic acid may be oxidized with sodium periodate to create reactive aldehyde groups within the polymer chain. The aldehyde groups may then react with primary amine groups in a tissue-based membrane forming imine bonds and a membrane/hydrogel polymer complex. The remaining reactive groups (aldehyde) may then be reduced to alcohol groups. Example suitable reducing agents may include, but are not limited to, sodium cyanoborohydride. Other reducing agents that may be employed in connection with the present disclosure, in certain instances, may include sodium tri-acetoxy-borohydride, sodium borohydride (especially the sodium salts of these ions), formamide, solid zinc, ascorbic acid, sodium thiosulfate, and sodium dithionite.

In a further embodiment consistent with the present disclosure, poly-cationic polymer may be further added on top of at least one portion of the poly-anionic hydrogel polymer/membrane complex. Alternatively, the order of application may be reversed (e.g. poly-cationic polymer then poly-anionic).

Figure 4:
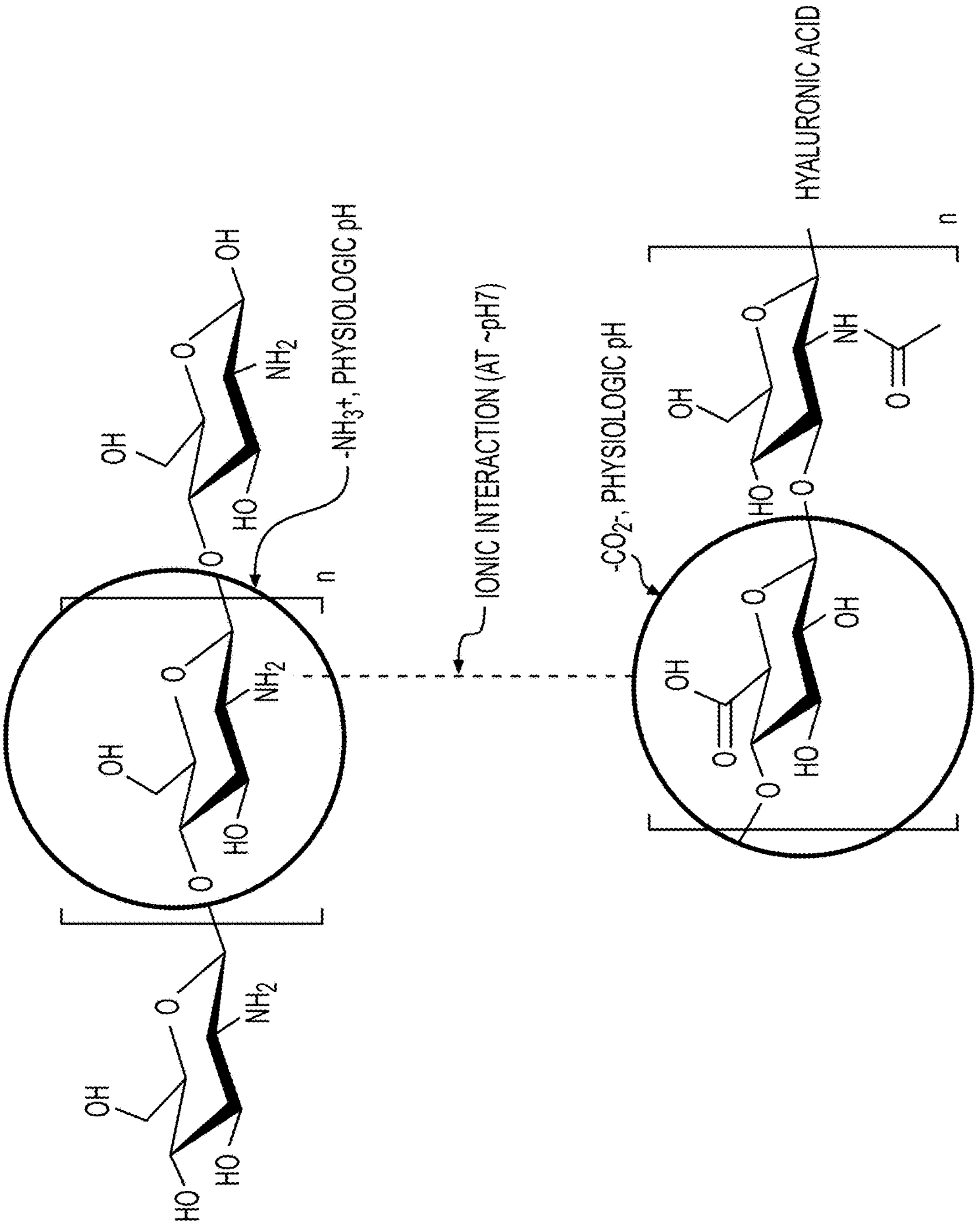
FIG. 4 is an illustrative example of poly-electrolyte complexation that may occur when a positively charged polymer ionically interacts with a negatively charged polymer to result in a solid/gel, according to an example embodiment.

Poly-electrolyte complexation may occur when a positively charged polymer ionically interacts with a negatively charged polymer to result in a solid/gel. This may occur with chitosan and hyaluronic acid at physiological conditions, as generally shown in FIG. 4.

Figure 5:
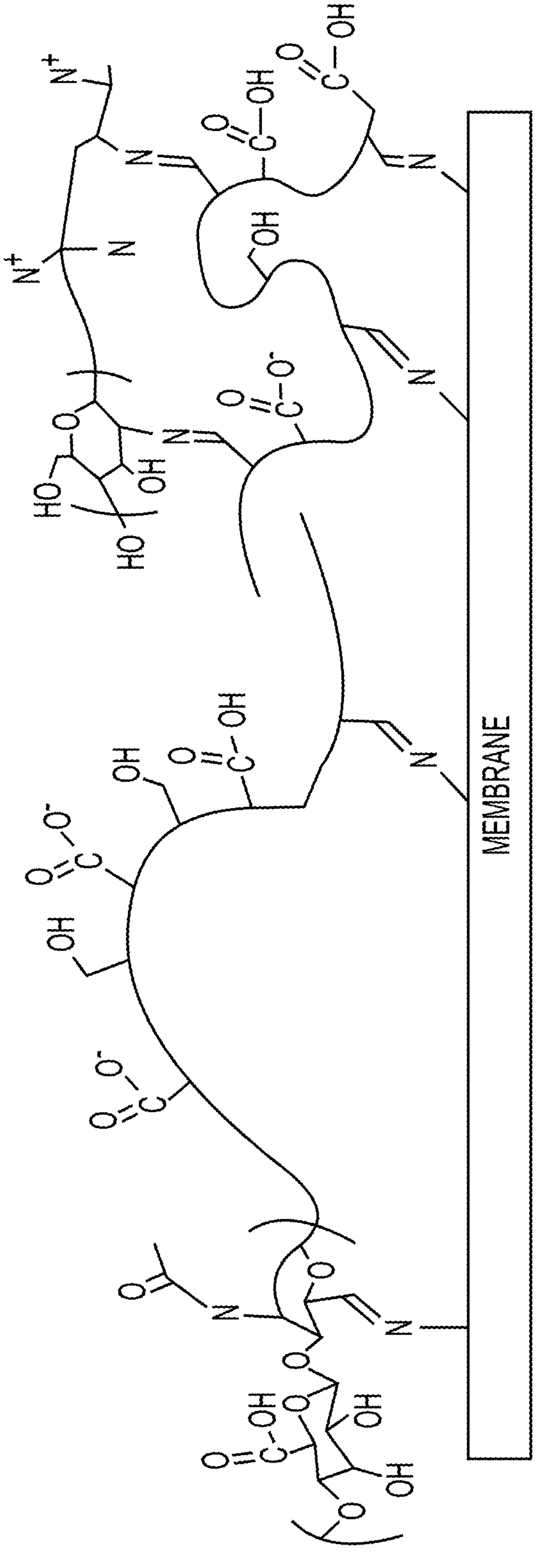
FIG. 5 is an illustrative example of hydrogel polymer/membrane and poly-cationic polymer complexation, according to an example embodiment.

Hyaluronate modified to include aldehyde groups (such as sodium formyl hyaluronate, shown in FIG. 5), may be sequentially reacted with the membrane and then the chitosan. This may create imine linkages between the hyaluronic acid and the surface of the membrane (and also possibly within the bulk of the membrane), and also imine linkages between the chitosan and the hyaluronic acid surface modified membrane. Poly-electrolyte complexation may also occur. FIG. 5 generally depicts an embodiment consistent with the present disclosure including the hydrogel polymer-membrane and poly-cationic polymer complexation.

Not all carboxylic acid and primary amine groups will be suitably ionized at physiological conditions. Reagents may be needed to adjust the pH, or other qualities of the formation solution to provide the necessary reaction conditions. The residual aldehyde groups of hydrogels, such as oxidized hyaluronic acid, may be neutralized, if desired, by a variety of chemistries. In one example embodiment, the aldehydes may be reduced to alcohol groups by reacting with a reducing agent, such as sodium tri-acetoxy-borohydride. Other suitable reducing agents, in certain instances, may include, but are not limited to, sodium tri-acetoxy-borohydride, sodium borohydride (especially the sodium salts of these ions), formamide, solid zinc, ascorbic acid, sodium thiosulfate, and sodium dithionite.

In some further illustrative example embodiments, the neutralization may be conducted with a small molecule amine, for example glycine, resulting in additional imine bonds, or sulfur based reducing agents, such as sodium bisulfite or sodium dithionite, which generate bisulfite adducts. An additional benefit of the bisulfite adducts may be that they can also participate in the poly-electrolyte complexation.

The molecular weight of the poly-cation and poly-anion polymers may influence the binding strength of the membrane-polymer complex. Specifically, larger molecular weights may correlate with increased interaction and binding force. Example molecular weights of the poly-anionic polymer range from 10,000 Da to over 4,000,000 Da. In some embodiments, the molecular weights of the poly-anionic polymer range from 1,000,00 to 2,000,000 Da. Example molecular weights of the poly-cationic polymer range from 10,000 Da to over 4,000,000 Da. In some embodiments, the molecular weights of the poly-cationic polymer range from 80,000-120,000 Da. Additionally, branched or cross-linked polymers with increased molecular weight may also be used.

With regard to hyaluronic acid in particular, the molecular weight may be an important feature of the cellular interactions/biocompatibility of the polymer-membrane complex.

Adjusting the degree of substitution, such as the number of aldehydes per molecule, may influence the average size of the hyaluronic acid fragments complexed. In some embodiments, molecular weights in the range of greater than or equal to about 1000 k Daltons may be are associated with preventing inflammation and cell migration. Smaller molecular weight fragments, particularly polymers with molecular weights less than about 10 k Daltons may be associated with promoting angiogenesis and wound healing. These lower molecular weight polymers may also be associated with increased inflammation. The largest molecular weight polymers may, in some embodiments, provide bio-regeneration advantages in view of the many enzymes that are common in the extracellular environment, which may continue to reduce the polymer the fragment size.

Additionally, in some embodiments, higher molecular weight aldehyde modified molecules may have larger hydraulic radii, which may enable the polymer to have a higher degree of interaction and binding with the membrane surface. In contrast, lower molecular weight polymers may, in some situations, penetrate the membrane to a higher degree.

Consistent with the foregoing, in general the present disclosure may generally provide tissue repair membranes that may uniquely be self-adhering (i.e., the tissue repair membrane may adhere to itself), while exhibiting little adhesiveness to surrounding or adjacent matter, e.g., tissue, and/or even providing a lubricating effect and/or relatively low coefficient of friction between the tissue repair membrane and surrounding or adjacent matter, e.g., tissue. In some implementations, the tissue repair membrane may include poly-anionic surface regions and poly-cationic surface regions on the tissue repair membrane. In some implementations, these poly-anionic and poly-cationic surface regions may form poly-electrolyte complexes when they are brought into contact with each other. The interaction between positive and negative charged groups may provide for preferential adhesion of the tissue repair membrane to itself, with limited if any adhesion to surrounding or adjacent matter, e.g., tissue. In some implementations, the poly-anionic surface regions may act as a lubricating layer for the tissue repair membrane with respect to surrounding or adjacent, e.g., tissue (i.e., tissue contacted by the tissue repair membrane). When acting as a lubricating layer, the poly-anionic surface regions may, in some embodiments, decrease the friction and/or adhesiveness of the tissue repair membrane to surrounding, e.g., tissue (i.e., tissue contacted by the tissue repair membrane), while still allowing the tissue repair membrane to adhere to itself. As generally noted above, in some example embodiments, poly-electrolyte complexation may occur when a positively charged polymer ionically interacts with a negatively charged polymer, which may, in some implementations, result in a solid and/or gel material. In some example embodiments, poly-electrolyte complexation may occur between a poly-cationic polymer including chitosan and a poly-anionic polymer including hyaluronic acid at physiological conditions. As discussed above, other suitable poly-cationic polymers and poly-anionic polymers may also be used to achieve desirable performance.

Consistent with some embodiments, hydrogel polymers herein, including one or more of poly-cationic polymers and poly-anionic polymers may be used in connection with implementations other than tissue repair matrices. For example, in some embodiments, hydrogel polymers described herein may be used to treat and/or coat at least a portion of fabrics, gauze, other types of materials that may be used in connection with nerve repair and/or in connection with other treatment fields or endeavors. In such implementations, the hydrogels may be applied to any suitable substrate. Example substrates may include natural and/or synthetic materials, including polymeric materials, films, fabrics, paper, and the like. Substrates coated with the hydrogel materials may provide self-adhesive characteristics, while exhibiting little adhesiveness to surrounding or adjacent matter, and/or even providing a lubricating effect and/or relatively low coefficient of friction between the coated material and surrounding or adjacent matter.

The lubricity of example formulations was experimentally evaluated by testing the static coefficient of friction of a test membrane treated with sample formulations against a cellulose sheet. For the purpose of experimentation, a small intestine submucosa (SIS) sheet consistent with Axoguard Nerve Protector, available from Axogen Corporation, was used as a test membrane and printing paper was used as a cellulose sheet substrate to simulate tissue. The SIS membrane was used as-is (no applied test formulation) and with various formulations including hyaluronic acid, alginic acid, and/or chondroitin sulfate. The SIS membrane (as is and/or treated with a test formulation) was hydrated for approximately 15 seconds in saline solution (approximately 0.9% NaCl by weight) containing calcium chloride at a physiological concentration (about 1.3 mM), and wrapped around a metal block. The SIS membrane (treated and untreated) was placed on top of the cellulose sheet submerged in the saline and calcium chloride solution, and a hanging mass holder was attached to the block using a string-pulley system. Small amounts of mass (in the form of water) were added to the mass holder using a pipette until the point at which the block (including the SIS membrane positioned against the cellulose sheet) began to slide across the cellulose sheet. The weight of the mass holder plus the added water was recorded and the coefficient of static friction was calculated as: coefficient of static friction=mass (hanging)/mass (heavy block). Evaluations of the coefficient of static friction were conducted at Day 0, with the SIS membrane (untreated and treated) hydrated for approximately 15 seconds in the saline solution including calcium chloride and tested against the cellulose surface. Evaluations of the coefficient of static friction were also conducted at Day 1, with SIS membrane (untreated and treated) left soaking in the saline solution including calcium chloride for 24 hours at 4 degrees C.

Test samples of different test formulations were prepared by submerging approximately 3.5×5 cm SIS membranes in a 50 ml conical tube containing about 40 ml of the desired formulations at 4 degrees C. for about 27 hours. After 27 hours, the membranes were removed from the formulations and placed on a Tyvek sheet, and covered with another Tyvek sheet. The membranes were then placed in a vacuum oven and covered with a conformable set at 15 mbar pressure and 35 degree C. overnight to allow the formation of a thin dry layer of the lubricant formulation. Two layers of silicone pads (approximately 5 mm thickness for each) were added on top of the Tyvek sheets to keep the membranes flat during drying. Excess dried lubricant was removed from the edges of the membranes. The membranes were then stored in air-tight containers and stored at 4 degrees C. until use.

Figure 6:
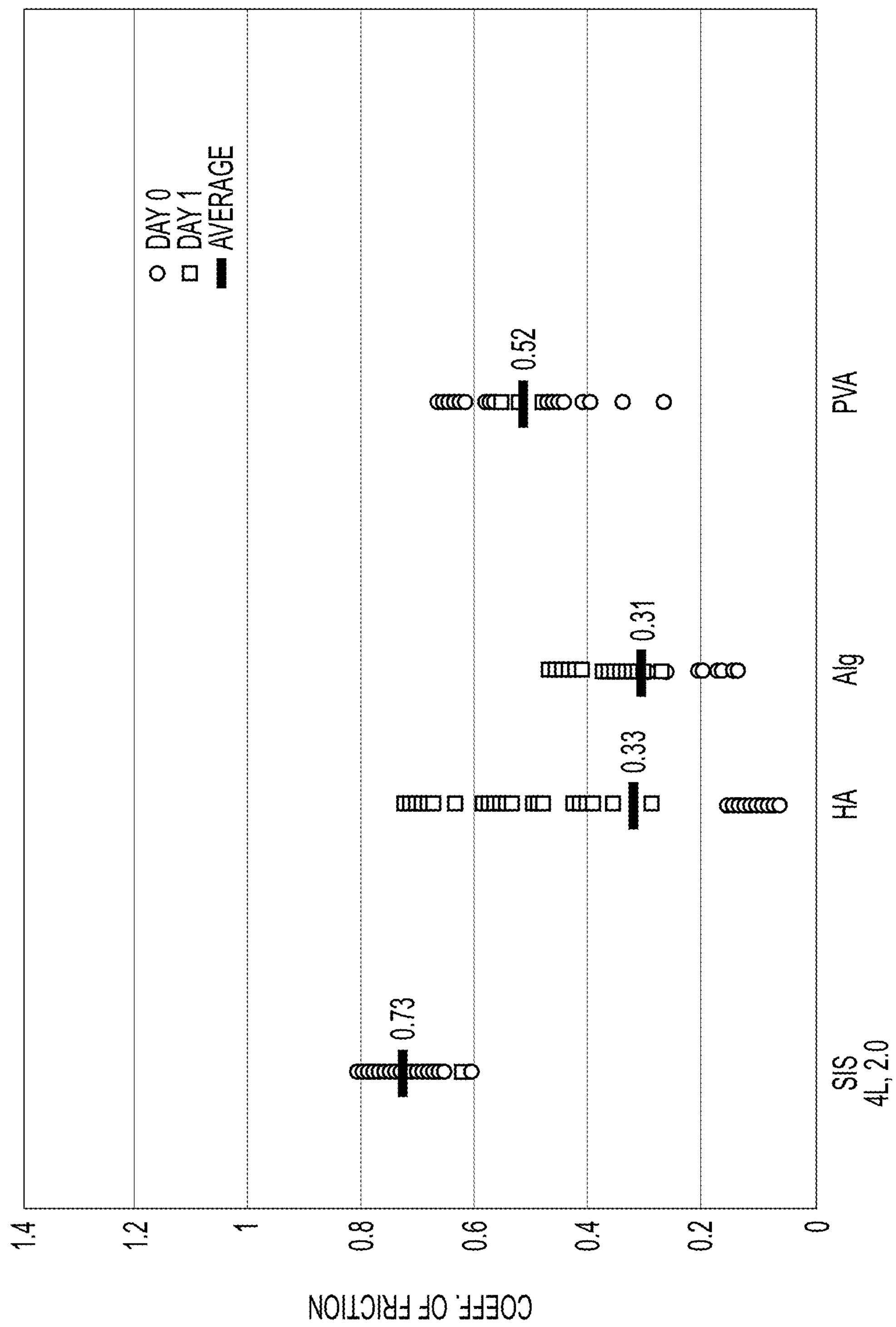
FIG. 6 is a charter showing experimental evaluation of coefficient of static friction for several test samples, according to an example embodiment.
Figure 7:
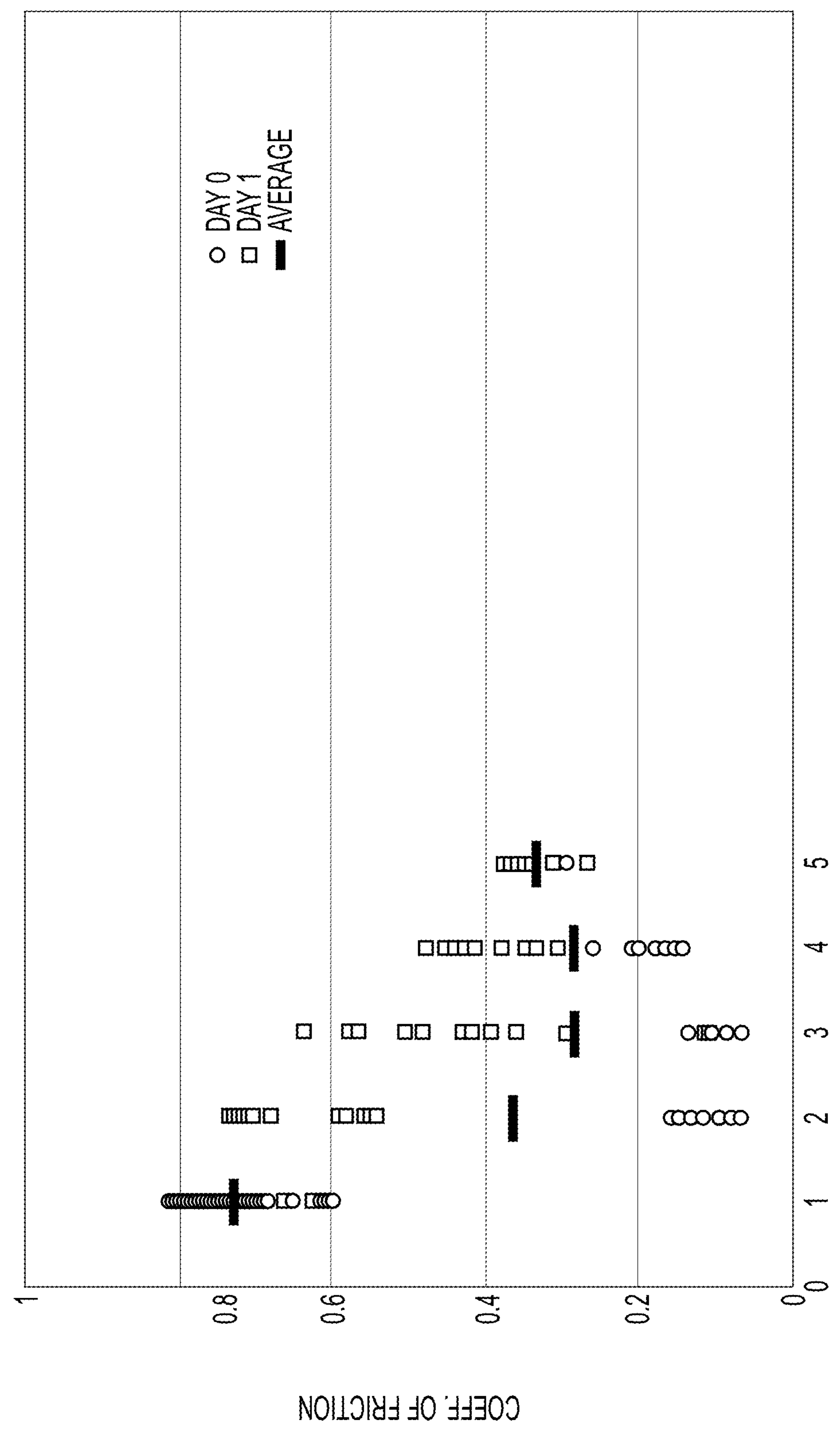
FIG. 7 is a chart showing experimental evaluation of coefficient of static friction for several test samples, according to an example embodiment.

As shown in FIG. 6, hyaluronic acid demonstrated a greater reduction in coefficient of static friction than alginate, as compared to untreated SIS. However alginate demonstrated better retention of lubricating properties, as exhibited by a comparison of Day 0 results versus Day 1 results. Both hyaluronic acid and alginate demonstrated greater lubricating properties than PVA as a reference material. Additionally, as shown in FIG. 7 and Table 1 below, higher molecular weight hyaluronic acid (HMW HA tested=1.0-1.5 million Daltons) demonstrated a greater retention of lubricating properties than lower molecular weight hyaluronic acid (LMW HA tested=0.8-1.0 million Daltons), as exhibited by a comparison of Day 0 results versus Day 1 results. Additionally, a higher viscosity alginate (MV ALG tested=1320 MPA at 1% aqueous solution) demonstrated longer retention of lubricating properties as compared to low viscosity alginate (LV ALG tested=≥2,000 CP at 2% aqueous solution). The results charted in FIG. 7 reference formulation numbers identified in Table 1.

TABLE 1

Static Coefficient of Friction for Test Formulations - Average of Day 0 and Day 1

| | | AVG |
|---|---|---|
| 1 | UNTREATED SIS (4 L-2.0) | 0.726 |
| 2 | 2% HA (LMW) | 0.367 |
| 3 | 2% HA (HMW) | 0.285 |
| 4 | 2% ALG (LV) | 0.289 |
| 5 | 2% ALG (MV) | 0.333 |

Consistent with some embodiments of the present disclosure, membranes having a relatively high degree of lubricity may be provided by way of physical interpenetrations of the polymers into the membrane substrate. For example, the membrane substrate, such as SIS or other suitable substrate, may be soaked in a formulation of hyaluronic acid and alginate. Higher solids content of the solutions may result in a more viscous solution which may become difficult handle and apply. Membranes may be exposed to solutions for sufficient time for the polymers to at least partially diffuse into the membrane. This time will be influenced by the molecular weight of the polymers with larger molecular weights diffusing more slowly, and the pore size of the membrane substrate with larger pores requiring less diffusion time. However, in most cases, there will be little risk of extending solution incubation past the minimum time. Solvent and pH of the polymer solution should be selected so that the polymers are soluble. If an ionic gelling polymer is used, care should be taken to avoid calcium or other multivalent cations during soaking as the solution may gel prematurely. In the case of 2% MV (medium viscosity) alginate and 2% HMW (high molecular weight) hyaluronate in water, hydration with the polymer solution appears to occur rapidly (e.g., within 20 min in some embodiment) but may be extended to approximately 27 hrs at 4 C to ensure consistency and saturation. Once the membrane substrate has been saturated with the formulation of hyaluronic acid and alginate to a desired degree, the membrane substrate may be dried. In some embodiments, the alginate may provide some degree of ionic cross-linking in the presence of calcium ions and/or other divalent cations. Examples of divalent cation sources include but are not limited to calcium chloride, calcium acetate, magnesium chloride, and magnesium acetate. In some embodiments, the ionic cross-linking may improve the retention of the hyaluronic acid and alginate over time, and may provide increased lubricity for the treated membrane over time, as compared to embodiments with lower degrees, or no, ionic cross-linking.

Figure 8:
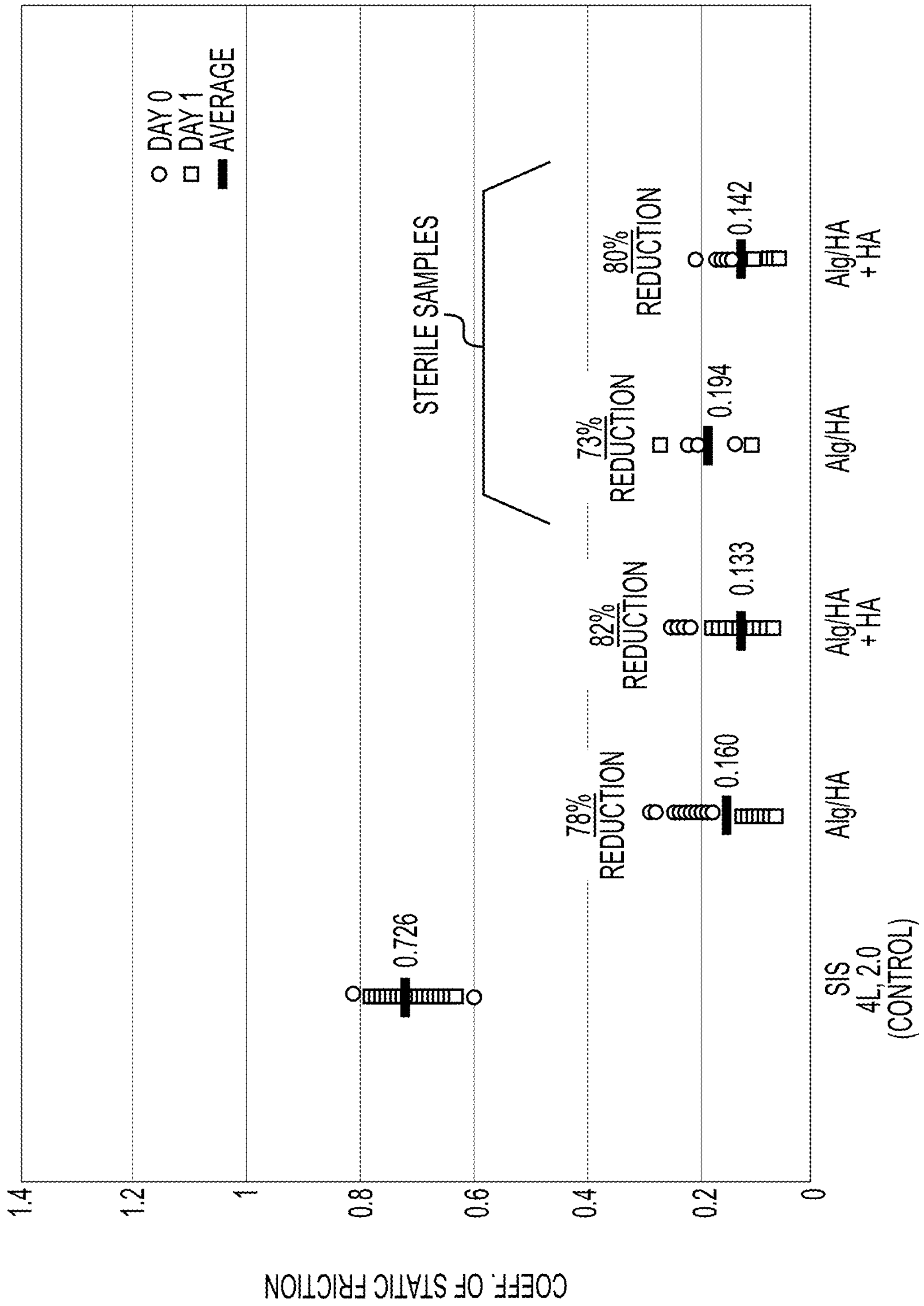
FIG. 8 is a chart showing experimental evaluation of coefficient of static friction for several test samples, according to an example embodiment.

Referring to FIG. 8, a comparison of formulations including a combination of hyaluronic acid and alginate (Alg/HA)

is shown at Day 0 and Day 1. Additionally, the depicted comparison includes a bi-layer coating formed from an initial coating of hyaluronic acid and alginate applied to the membrane substrate (e.g., SIS), with an additional layer of hyaluronic acid applied over the initial coating (Alg/HA+HA). The hyaluronic acid and alginate coatings may be formed in a generally similar manner as described above (e.g., soaking the SIS, or other, membrane in a solution of the desired formulation, and subsequently drying the coated membrane). In an example embodiment, the bi-layer coating may be formed by soaking the dried membrane including the hyaluronic acid and alginate coating in a solution of hyaluronic acid. The viscosity of the solution for the second coating may desirably be low enough to allow even coating of the membrane and may limit the total solids content of the solution. As the second hydrogel layer only needs to interact with the $1^{st}$ hydrogel layer and does not need to diffuse into the membrane substrate, a shorter incubation time could be used. In one instance, a 2% solution of high molecular weight sodium hyaluronate in water can be applied for approximately 2 min, although other durations may be used to provide acceptable coating. The coefficient of static friction was evaluated in a manner generally corresponding to the previous testing protocol. As shown, the hyaluronic acid and alginate coated membrane provides improved lubricity (e.g., as compared to the single component coatings described with respect to FIGS. 6 and 7 and Table 1).

Additionally, the bi-layer configuration provided a further increase in lubricity. In some embodiments, the improved lubricity of the hyaluronic acid and alginate coating over time (e.g., as compared to single component coatings) may be provided by the slow release of hyaluronic acid interlocked between alginate hydrogel. Additionally, in some embodiments, the improved lubricity of the bi-layer coating may arise from the initial lubricity provided by the outer layer of hyaluronic acid.

Figure 9:
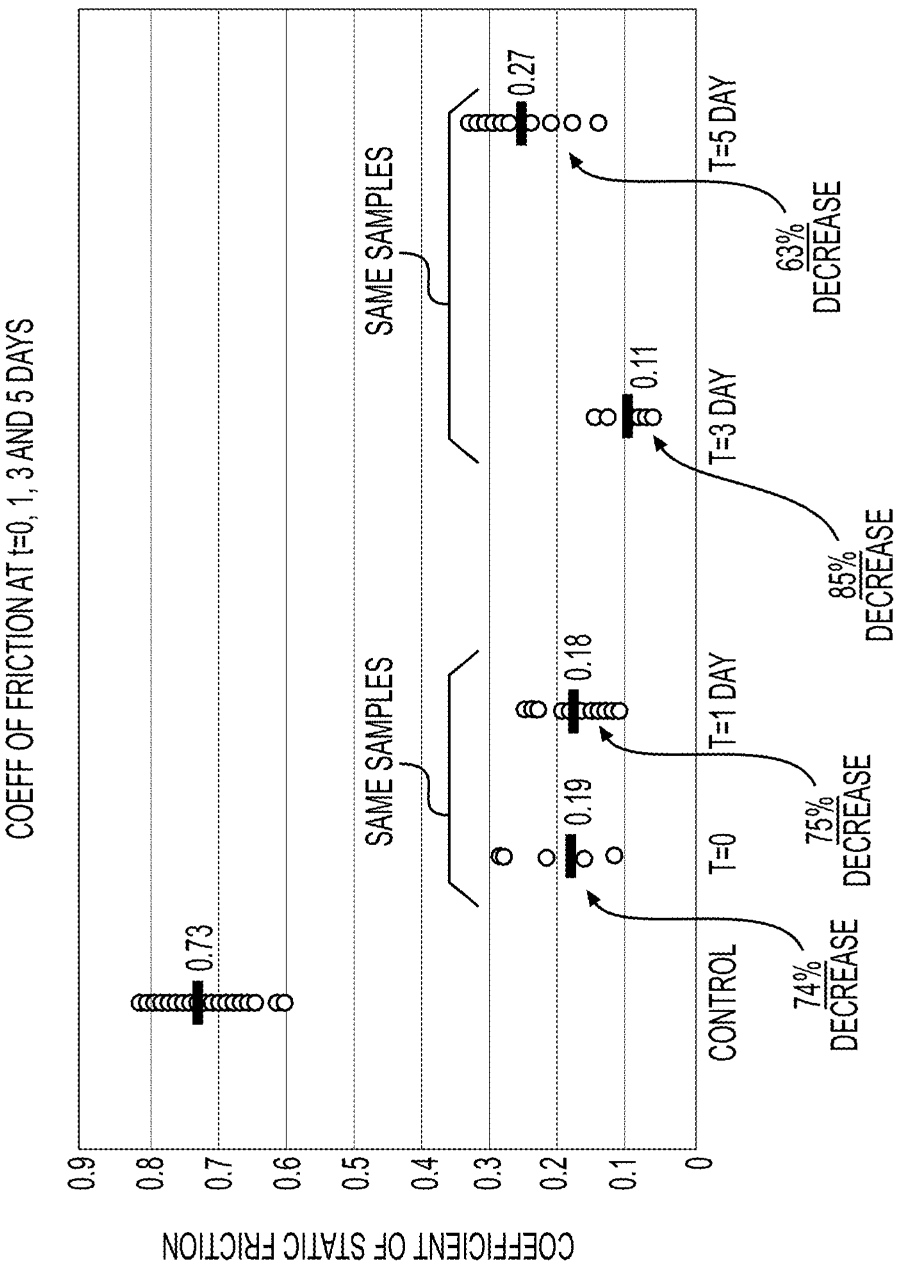
FIG. 9 is a chart showing experimental evaluation of coefficient of static friction for several test samples, according to an example embodiment.

Referring also to FIG. 9, the lubricity over an extended time is shown for coatings including the hyaluronic acid and alginate coatings discussed with respect to FIG. 8. In the depicted embodiment, samples were tested at 0, 1, 3, and 5 days after initial hydration, in which one set of samples were tested at Day 0 and Day 1, and a second set of samples were tested at Day 3 and Day 5. When not being tested, the samples were stored in solutions of 0.9% NaCl with 1.3 mM $CaCl_2$) at 4-8° C. As shown, the membrane coated with hyaluronic acid and alginate demonstrated significantly improved lubricity over the extended time period of testing, as compared to the untreated SIS control sample.

Continuing with the foregoing, in some example embodiments a tissue repair membrane may be formed from more than one layer of a membrane substrate, such as SIS. In a particular illustrative embodiment, the tissue repair membrane may include 4 layers of SIS, however it will be appreciated that a greater or fewer number of layers may be utilized (e.g., 1-8 layers, 2-6 layers, 2-4 layers, etc. as well as various additional included ranges of layers). In an embodiment, the layers of SIS may be soaked in a solution of 2% alginate and 2% hyaluronic acid (e.g., which may be provided in various forms, such as sodium hyaluronate), in which the solution concentrations indicate a weight percent relative to the total weight of the solution. It will be appreciated that other solution concentrations may be utilized, and that the relative concentration of alginate an hyaluronate need not be the same. Range of alginate and hyaluronicacid concentrations may be between ~0.5 and 5%, however combinations may be solubility limited in the higher end of the range. The layered SIS soaked in the solution may be subsequently dried, resulting in a coating on both sides of the layered SIS membrane. The "sol" gel soaking into the membrane may provide for some interpenetration of the polymer chains of the alginate/hyaluronic acid and the SIS collagens. Exposure to calcium ions, either during the manufacturing process and/or during subsequent hydration of the dried tissue repair membrane (e.g., at the time of use) may ionically crosslink the alginate, which may aid in retaining the gel layer.

In some embodiments, the SIS membrane base may provide desirable handling properties. For example, the tissue repair membrane may be readily moved and handled in the surgical field. Additionally, the SIS membrane may allow the tissue repair membrane to be secured by sutures or clips. Additionally, remodeling of the SIS may also occur, similar to other SIS based products, and can result in new connective tissue layers in the right use cases.

Consistent with some embodiments of the present disclosure, high molecular weight hyaluronic acid (e.g. 1 million Dalton or more) may provide an extremely biocompatible lubricating layer (e.g., as the hyaluronic acid molecule is exactly/substantially the same as is present in human tissue naturally). Alginate may also provide some lubricity on its own.

Further, alginate may perform as an ionically crosslinking polymer that may facilitate retaining the hyaluronate at the site of implant for a longer period. The hydrogel film that forms may act as a lubricating layer reducing the forces seen by the gliding tissue. The gel also may also act as a temporary barrier layer, and the gel will typically dissolve in days to weeks (e.g., dissolve in 7-10 days in some embodiments). This temporary barrier may provide at least two notable benefits. First it may physically separate tissues during early healing, which may prevent early soft tissue attachments that may develop over time, especially when the injury that the tissue repair membrane is used in connection with is splinted, which prevents normal motion and tissue gliding and may increase the risk of soft tissue attachments. Additionally, the temporary barrier may provide for a degree of self-sizing of the nerve wrap product (i.e., the tissue repair membrane) as the gel layer is deformable. For example, if a nerve swells after a tourniquet is removed or during early healing, the gel layer may "squeeze" out of the nerve wrap product, which may prevent and/or reduce the degree of compression of the nerve (as long as the thickness of the gel layer is not exceeded). Both hyaluronic acid and alginate are substantially non-adhesive to cells.

According to some embodiments, a tissue repair membrane including hyaluronic acid may provide a wide array of possible benefits and applications. For example, the tissue repair membrane may aid in maintaining tissue planes and long-term tissue gliding. For example, this aspect may be, at least in part, facilitated by the ability of SIS remodel into a new connective tissue layer. Additionally, in some situations a tissue repair membrane consistent with the present disclosure may improve options for early mobilization (e.g., by reducing friction forces and reducing risk of irritation or rupture). Further, in some situations a tissue repair membrane consistent with the present disclosure may also improve options for late mobilization (e.g., by providing a temporary layer that may help prevent early attachment formation while splinted), depending on surgical circumstances and patient needs. In some implementations, a tissue repair membrane consistent with the present disclosure may aid in preventing and/or reducing nerve compression if nerve swells after a tourniquet is removed or during early healing, e.g., by the deformation of the gel layer. In some implementations, the lubrication provided by a tissue repair membrane consistent with the present disclosure may also be "tacky" (paradoxical behavior of some lubricants, such as shear thinning fluids), which may help in surgical placement, as the tissue repair membrane may tend to stay where it is placed (e.g., by exhibiting a high zero shear viscosity), but may still reduce frictional forces (e.g., by exhibiting low viscosity under shear). Various additional benefits and advantages may be provided by tissue repair membranes consistent with the present disclosure.

The foregoing description and examples have been set forth merely to illustrate the present disclosure and are not intended to be limiting. Since modifications of the described embodiments incorporating the spirit and substance of the disclosure may occur to persons skilled in the art, the disclosure should be construed broadly to include all variations within the scope of this application, including but not limited to the appended claims and equivalents thereof.

The invention claimed is:

1. A tissue repair membrane consisting of:

a tissue repair membrane substrate formed of a multi-layer sheet; and a layer of hydrogel polymer coating on the tissue repair membrane substrate, wherein the hydrogel polymer coating is formed from a solution of hyaluronic acid and alginate, a concentration of each of the hyaluronic acid and the alginate being 0.5% to 5% by weight.

2. The tissue repair membrane of claim 1, wherein the layer of hydrogel polymer coating further comprises a poly-anionic polymer selected from the group consisting of chondroitin, oxidized cellulose, heparin, dermatan, sulfated or otherwise modified versions of the prior polymers and combinations thereof.

3. The tissue repair membrane of claim 1, wherein the layer of hydrogel polymer coating is not covalently bound to the tissue repair membrane substrate.

4. The tissue repair membrane of claim 1, wherein the layer of hydrogel polymer coating is present on a majority of both sides of the tissue repair membrane substrate.

5. The tissue repair membrane of claim 1, wherein the concentration of hyaluronic acid is the same as the concentration of alginate.

6. The tissue repair membrane of claim 1, wherein the concentration of at least one of hyaluronic acid or alginate is 2% by weight.

7. The tissue repair membrane of claim 1, wherein the multi-layer sheet has from two layers to six layers.

8. The tissue repair membrane of claim 1, wherein the multi-layer sheet has from two layers to four layers.

9. The tissue repair membrane of claim 1, wherein the layer of hydrogel polymer coating is configured to dissolve in seven to ten days.

10. The tissue repair membrane of claim 1, wherein the tissue repair membrane substrate is formed from human placental tissue or human cadaver tissue.

11. The tissue repair membrane of claim 1, wherein the tissue repair membrane substrate is formed of animal tissue.

12. The tissue repair membrane of claim 1, wherein the tissue repair membrane substrate is formed of natural or synthetic polymers.

13. The tissue repair membrane of claim 1, wherein the tissue repair membrane substrate is formed of woven materials.

14. The tissue repair membrane of claim 1, wherein the tissue repair membrane substrate is formed of small intestine submucosa.

15. The tissue repair membrane of claim 1, wherein the layer of hydrogel polymer coating at least partially physically interpenetrates the tissue repair membrane substrate.

16. The tissue repair membrane of claim 1, wherein the hyaluronic acid has a molecular weight of 1.0 to 1.5 million Daltons.

17. A tissue repair membrane consisting of:

a tissue repair membrane substrate formed of a multi-layer sheet, wherein the multi-layer sheet comprises two to six layers of animal or human tissue; and a layer of hydrogel polymer coating on the tissue repair membrane substrate, wherein the hydrogel polymer coating is formed from a solution of at least one of hyaluronic acid having a concentration of 0.5% to 5% by weight, or alginate having a concentration of 0.5% to 5% by weight.

18. The tissue repair membrane of claim 17, wherein the layer of hydrogel polymer coating further comprises a poly-anionic polymer selected from the group consisting of chondroitin, oxidized cellulose, heparin, dermatan, sulfated or otherwise modified versions of the prior polymers and combinations thereof.

19. The tissue repair membrane of claim 17, wherein the layer of hydrogel polymer coating is not covalently bound to the tissue repair membrane substrate.

20. The tissue repair membrane of claim 17, wherein the layer of hydrogel polymer coating covers both sides of the tissue repair membrane substrate.

21. The tissue repair membrane of claim 17, wherein the multi-layer sheet comprises two to four layers of animal or human tissue.

22. The tissue repair membrane of claim 17, wherein the layer of hydrogel polymer coating is configured to dissolve in seven to ten days.

23. The tissue repair membrane of claim 17, wherein the tissue repair membrane substrate is formed from human placental tissue or human cadaver tissue.

24. The tissue repair membrane of claim 17, wherein the tissue repair membrane substrate is formed of small intestine submucosa.

25. The tissue repair membrane of claim 17, wherein the layer of hydrogel polymer coating at least partially physically interpenetrates the tissue repair membrane substrate.

26. The tissue repair membrane of claim 17, wherein the hyaluronic acid has a molecular weight of 1.0 to 1.5 million Daltons.

27. The tissue repair membrane of claim 17, wherein the concentration of the at least one of hyaluronic acid or alginate is 2% by weight.

28. The tissue repair membrane of claim 1, wherein the concentration of hyaluronic acid is different from the concentration of alginate.

29. The tissue repair membrane of claim 17, wherein the concentration of hyaluronic acid is the same as the concentration of alginate.

* * * * *